US012617750B2

(12) United States Patent
Huchede et al.

(10) Patent No.: US 12,617,750 B2
(45) Date of Patent: May 5, 2026

(54) PROCESS FOR THE PREPARATION OF HEXAMETHYLENEDIAMINE BY HYDROGENATION OF ADIPONITRILE IN THE PRESENCE OF RANEY NICKEL AND A BASIC CO-CATALYST

(71) Applicant: BASF SE, Ludwigshafen am Rhein (DE)

(72) Inventors: Maxime Huchede, Lyons (FR); Sandra Chouzier, Deaux (FR)

(73) Assignee: BASF SE, Ludwigshafen am Rhein (DE)

( * ) Notice: Subject to any disclaimer, the term of this patent is extended or adjusted under 35 U.S.C. 154(b) by 760 days.

(21) Appl. No.: 17/913,177

(22) PCT Filed: Mar. 24, 2021

(86) PCT No.: PCT/EP2021/057591
§ 371 (c)(1),
(2) Date: Sep. 21, 2022

(87) PCT Pub. No.: WO2021/191289
PCT Pub. Date: Sep. 30, 2021

(65) Prior Publication Data
US 2023/0128673 A1     Apr. 27, 2023

(30) Foreign Application Priority Data
Mar. 25, 2020    (EP) ..................................... 20165609

(51) Int. Cl.
*C07C 209/48*     (2006.01)
*B01J 23/04*      (2006.01)
*B01J 25/02*      (2006.01)

(52) U.S. Cl.
CPC ............. *C07C 209/48* (2013.01); *B01J 23/04* (2013.01); *B01J 25/02* (2013.01)

(58) Field of Classification Search
None
See application file for complete search history.

(56) References Cited

U.S. PATENT DOCUMENTS

| | | | |
|---|---|---|---|
| 5,777,166 A | | 7/1998 | Cordier et al. |
| 6,281,388 B1 | | 8/2001 | Goodwin et al. |
| 6,376,714 B1 | | 4/2002 | Allgeier et al. |
| 6,660,887 B1 | | 12/2003 | Ward et al. |
| 2003/0144552 A1 | | 7/2003 | Boschat et al. |
| 2004/0147784 A1 | | 7/2004 | Ward et al. |
| 2006/0122433 A1 | | 6/2006 | Vandenbooren et al. |
| 2015/0025266 A1 | | 1/2015 | Henri et al. |

FOREIGN PATENT DOCUMENTS

| | | |
|---|---|---|
| CN | 1141031 A | 1/1997 |
| CN | 1335833 A | 2/2002 |
| CN | 1745059 A | 3/2006 |
| CN | 1747925 A | 3/2006 |
| CN | 103977819 A | 8/2014 |
| CN | 104245653 A | 12/2014 |
| JP | 46-008283 B1 | 3/1971 |
| JP | 2002-533319 A | 10/2002 |
| JP | 2003-525924 A | 9/2003 |
| JP | 2004-534778 A | 11/2004 |

OTHER PUBLICATIONS

International Search Report and Written Opinion received for PCT Patent Application No. PCT/EP2021/057591, mailed on Jun. 15, 2021, 9 pages.

*Primary Examiner* — Renee Claytor
*Assistant Examiner* — Jennifer C Sawyer
(74) *Attorney, Agent, or Firm* — Faegre Drinker Biddle & Reath LLP

(57)          ABSTRACT

The present invention relates to a process for the preparation of hexamethylenediamine by hydrogenation of adiponitrile in the presence of a Raney nickel catalyst and a basic co-catalyst containing potassium hydroxide, wherein the basic co-catalyst contains a further basic compound selected from the group consisting of alkaline hydroxides, alkaline earth hydroxides and ammonium hydroxides.

14 Claims, No Drawings

PROCESS FOR THE PREPARATION OF HEXAMETHYLENEDIAMINE BY HYDROGENATION OF ADIPONITRILE IN THE PRESENCE OF RANEY NICKEL AND A BASIC CO-CATALYST

CROSS-REFERENCE TO RELATED APPLICATIONS

This application is a national stage application (under 35 U.S.C. § 371) of PCT/EP2021/057591, filed Mar. 24, 2021, which claims benefit of European Application No. 20165609.7, filed Mar. 25, 2020, both of which are incorporated herein by reference in their entirety.

TECHNICAL FIELD

The present invention relates to a process for the preparation of hexamethylenediamine by hydrogenation of adiponitrile in the presence of a Raney nickel catalyst and a basic co-catalyst.

BACKGROUND ART

Hexamethylenediamine is a compound used in numerous applications, the main ones of which are the manufacture of polyamides such as poly(hexamethylene adipamide), more commonly known as PA 6,6, and the manufacture of hexamethylene diisocyanate.

Several processes for manufacturing hexamethylenediamine have been proposed, which generally consist of a hydrogenation of adiponitrile (tetramethylene dicyanide) in the presence of a hydrogenation catalyst. Two types of process are utilized industrially that use different catalysts and different temperature and pressure conditions.

Thus, a first type of hydrogenation process that is utilized and described in the literature consists in hydrogenating nitrile compounds in the presence of ammonia and under high pressure, with a ruthenium-based catalyst for example. Iron based catalysts under high pressure and temperature are also used.

A second type of process consists in carrying out the hydrogenation of nitrile compounds under pressure pressure and at a not very high temperature, for example at 25° C. and 80 bar, in the presence of a basic compound and a catalyst based on Raney nickel. In the latter type of process, the hydrogenation of nitrile compounds to amines takes place in the presence of a catalyst based on optionally doped Raney nickel. These catalysts are prepared by the leaching of aluminium, from Ni—Al alloys, in a strongly alkaline medium. The catalysts obtained are composed of agglomerates of nickel crystallites, having a high specific surface area and a variable residual aluminium content.

It is known that adiponitrile can react by hydrogenation to give a cyclic diamine, diaminocyclohexane (DCH). However, DCH is particularly troublesome since it has a boiling point close to the boiling point of the targeted amine and is therefore very difficult to separate.

There is an industrial need for optimization of the hydrogenation of adiponitrile to hexamethylenediamine, by means of Raney nickel catalysts, especially with respect to the activity, the selectivity and the deactivation behaviour of the final catalyst. In particular, it is important to limit the formation of diaminocyclohexane in order to obtain a hexamethylendiamine which can be purified with a minimum capital cost and a minimum energy consumption.

US 2003/0144552 A1 discloses the hydrogenation of adiponitrile to hexamethylene-diamine in the presence of Raney nickel doped with chromium in a solution containing hexamethylenediamine and KOH. The use of a further hydroxide is not described.

It is an object of the present invention to provide a process for the preparation of hexamethylenediamine by hydrogenation of adiponitrile in the presence of a Raney nickel catalyst which is characterized in a low formation of diaminocyclohexane (DCH) as side product.

SUMMARY OF THE INVENTION

The object is achieved by a process for the preparation of hexamethylenediamine by hydrogenation of adiponitrile in the presence of a Raney nickel catalyst and a basic co-catalyst containing potassium hydroxide, wherein the basic co-catalyst contains a further basic compound selected from the group consisting of alkaline hydroxides, alkaline earth hydroxides and ammonium hydroxides.

DETAILED DESCRIPTION

Further alkaline hydroxides are hydroxides of Li, Na, Rb and Cs. Alkaline earth hydroxides are hydroxides of Mg, Ca, Sr and Ba.

In one embodiment, the basic co-catalyst contains cesium hydroxide CsOH as further basic compound.

In one preferred embodiment, the basic co-catalyst contains barium hydroxide $Ba(OH)_2$ as further basic compound.

In further preferred embodiments, the basic co-catalyst contains an ammonium hydroxide of the general formula $NR_4OH$, wherein each R is independently from each other an alkyl group having from 1 to 16 carbon atoms, preferably from 1 to 4 carbon atoms.

In particular preferred embodiments, each R in $NR_4OH$ is independently from each other methyl, ethyl, propyl or butyl.

In a very preferred embodiment, each R in $NR_4OH$ is methyl, i.e. the basic co-catalyst contains tetramethylammonium hydroxide as further basic compound.

In a further very preferred embodiment, each R in $NR_4OH$ is n-butyl, i.e. the basic co-catalyst contains tetra(n-butyl) ammonium hydroxide, as further basic compound.

Preferably, the basic co-catalyst contains from 50 to 95 mol-% of KOH and from 5 to 50 mol-% of the further basic compound. More preferably, the basic co-catalyst contains from 70 to 90 mol-% of KOH and from 10 to 30 mol-% of the further basic compound. In a particularly preferred embodiment, the basic co-catalyst contains from 75 to 85 mol-% of KOH and from 15 to 25 mol-% of the further basic compound.

The hydrogenation reaction is in general carried out in the presence of a solvent advantageously composed of the amine obtained by the hydrogenation. Thus, in the case of the hydrogenation of adiponitrile, hexamethylenediamine is advantageously used as main component of the reaction medium. The concentration of amine in the reaction medium is advantageously between 50% and 99% by weight, preferably between 60 and 99% by weight, of the liquid phase of the hydrogenation reaction medium.

The hydrogenation reaction is preferably carried out in the presence of water as other component of the reaction medium. This water is generally present in an amount of less than or equal to 50% by weight, advantageously of less than or equal to 20% by weight, in the liquid phase of the total reaction medium and more preferably between 0.1% and 15% by weight.

The amount of base added is determined in order to have at least 0.1 mol of base per kilogram of nickel, preferably between 0.1 and 2 mol of base per kg of nickel and more advantageously between 0.3 and 1.5 mol of base per kg of nickel.

For example, the hydrogenation can be carried out in hexamethylenediamine as solvent containing from 1 to 20% by weight, preferably from 5 to 15% by weight of an aqueous solution of the basic co-catalyst, based on the total amount of the reaction medium.

The hydrogenation reaction is in general carried out at a temperature of less than or equal to 150° C., e.g. from 50 to 150° C., preferably of less than or equal to 120° C. and more preferably of less than or equal to 100° C. The reaction temperature is most preferably from 50° C. to 100° C.

The hydrogen pressure in the reactor is in general from 1 to 100 bar (0.10 and 10 MPa), preferably from 10 to 50 bar (1 to 5 MPa).

The Raney nickel catalyst used according to the invention can advantageously comprise one or more other elements, often referred to as dopants, such as, for example, chromium, titanium, molybdenum, tungsten, manganese, vanadium, zirconium, iron, zinc and more generally the elements from groups IIB, IVB, IIIB, VB, VIB, VIIB and VIII of the Periodic Table of the Elements. Among these dopant elements, chromium, iron and/or zinc or a mixture of these elements are considered as being the most advantageous and are usually present at a concentration by weight (expressed relative to the Raney nickel metal) of less than 10%, preferably less than 5%. For example, the concentration of iron may be from 1 to 2% by weight, the concentration of chromium may be from 0.5 to 5% by weight and the concentration of zinc may be from 0.5 to 5% by weight.

Raney catalysts often comprise traces of metals present in the alloy used to prepare the said catalysts. Thus, aluminium is especially present in these catalysts. The concentration of aluminium may be from 2 to 10% by weight.

The optionally doped Raney Ni catalyst generally originates from a molten Ni—Al precursor alloy (Ni content for example from 28 to 59% by weight), to which metallic dopant elements, preferably iron, chromium and zinc, are added according to a doping procedure known as a "metallurgical" doping procedure. After cooling and grinding, the doped precursor alloy is subjected, in a conventional manner, to an alkaline attack that gives rise to a greater or lesser removal of aluminium and, optionally, of a fraction of the dopant element. The starting alloys used are, advantageously, chosen from the following forms of binary nickel/aluminium combinations: NiAl$_3$, Ni$_2$Al$_3$ and proeutectic Al/NiAl$_3$.

It is also possible to introduce dopants via "chemical" doping by impregnating the Raney Ni catalyst with a solution containing a precursor of the dopant element, by precipitating the dopant element on the Raney Ni catalyst, or by introducing the precursor compound of the dopant during the alkaline attack of the Raney alloy.

The present invention is further illustrated by the following examples. It should be understood that the following examples are for illustration purposes only, and are not used to limit the present invention thereto.

EXAMPLES

Example 1: General Procedure for Catalytic Activity Measurement

In a dry atmosphere of N$_2$, 0.48 g of nickel Raney catalyst were stirred with 7.3 g of water and 65.55 g of pure hexamethylenediamine and 55 μL of an aqueous solution of potassium hydroxide at 7 mol/L, corresponding to 0.8 mol of OH—/kg of Ni. The temperature was raised at 80° C. and 25 bar of hydrogen overall pressure. 2.5 g of adiponitrile (ADN) were added in one time in the autoclave and were hydrogenated. In those operating conditions, the catalytic activity is 111×10$^{-5}$ mol H$_2$/g$_{catalyst}$/s.

Example 2: General Procedure for Selectivity Measurement

In a dry atmosphere of N$_2$, 3 g of nickel Raney catalyst were stirred with 4.5 g of water and 40.5 g of pure hexamethylenediamine and 345 μL of an aqueous solution of potassium hydroxide at 7 mol/L, corresponding to 0.8 mol of OH—/kg of Ni. The temperature was raised at 80° C. and 25 bar of hydrogen overall pressure. 30 g of adiponitrile (ADN) were added dropwise at a mass flow of 10 g/h in the autoclave and were hydrogenated. After 3 hours, the crude hexamethylenediamine produced was analyzed by gas chromatography. 0.1812% of 1,2-diaminocyclohexane (DCH) were produced in those operating conditions.

Example 3: General Procedure for Catalyst Deactivation Measurement

At the end of ADN addition in the previous example, 2.5 g of ADN were added in one time in the autoclave containing the used catalyst and the crude HMD produced in example 2 (no emptying of the reaction mixture) and were hydrogenated (80° C., 25 bar). In those operating conditions, the catalytic activity is 44.6×10$^{-5}$ mol H$_2$/g$_{catalyst}$/s which represents 60% of activity loss (compared to 111×10$^{-5}$ mol H$_2$/g$_{catalyst}$/s).

Example 4: Modification of the Co-Catalyst for Catalytic Activity Measurement

The procedure of example 1 was followed except that 20 mol % of an aqueous solution of new co-catalyst (XOH) and 80 mol % of potassium hydroxide (KOH) aqueous solution were added in the reactor instead of 100% of KOH. The total amount of OH— remains 0.8 mol/kg of Ni.

The catalytic activities are reported in Table 1 below.

TABLE 1

| Co-catalyst | % mol of KOH/XOH | Activity (10$^{-5}$ molH$_2$/g/s) |
|---|---|---|
| KOH (100%, reference experiment) | 100/0 | 111 |
| CsOH | 80/20 | 106 |
| N(CH$_3$)$_4$OH | 80/20 | 125 |
| Ba(OH)$_2$ | 80/20 | 123 |
| NH$_4$OH | 80/20 | 96 |
| N(CH$_3$CH$_2$CH$_2$CH$_2$)$_4$OH | 80/20 | 94 |
| N(CH$_3$)$_3$BzOH | 80/20 | 71 |

Example 5: Modification of the Co-Catalyst for Selectivity Measurement

The procedure of example 2 was followed except that 20 mol % of an aqueous solution of new co-catalyst (XOH) and 80 mol % of potassium hydroxide (KOH) aqueous solution were added in the reactor instead of 100% of KOH. The total amount of OH— remains 0.8 mol/kg of Ni.

The weight percents of 1,2-diaminocyclohexane (DCH) in the crude hexamethylenediamine are reported in Table 2 below.

TABLE 2

| Co-catalyst | % mol of KOH/XOH | % of [DCH] | % of decrease |
|---|---|---|---|
| KOH (100%, reference experiment) | 100/0 | 0.1812 | x |
| CsOH | 80/20 | 0.1800 | −0.6% |
| N(CH$_3$)$_4$OH | 80/20 | 0.1380 | −24% |
| Ba(OH)$_2$ | 80/20 | 0.1723 | −4.9% |
| NH$_4$OH | 80/20 | 0.1910 | +5.4% |
| N(CH$_3$CH$_2$CH$_2$CH$_2$)$_4$OH | 80/20 | 0.1159 | −36% |
| N(CH$_3$)$_3$BzOH | 80/20 | 0.2196 | +21% |

Example 6: Modification of the Molar Percentage of XOH for Catalytic Activity Measurement The procedure of example 1 was followed except that 50 mol % of an aqueous solution of new co-catalyst (XOH) and 50 mol % of potassium hydroxide (KOH) aqueous solution were added in the reactor instead of 100% of KOH. The total amount of OH— remains 0.8 mol/kg of Ni.

The catalytic activities are reported in Table 3 below.

TABLE 3

| Co-catalyst | % mol of KOH/XOH | Activity (10$^{-5}$ molH$_2$/g/s) |
|---|---|---|
| KOH (reference experiment) | 100/0 | 111 |
| N(CH$_3$)$_4$OH | 80/20 | 125 |
| | 50/50 | 102 |

Example 7: Modification of the Molar Percentage of XOH for Selectivity Measurement The procedure of example 1 was followed except that 50 mol % of an aqueous solution of new co-catalyst (XOH) and 50 mol % of potassium hydroxide (KOH) aqueous solution were added in the reactor instead of 100% of KOH. The total amount of OH— remains 0.8 mol/kg of Ni.

The weight percent of 1,2-diaminocyclohexane in the crude hexamethylenediamine are reported in Table 4 below.

TABLE 4

| Co-catalyst | % mol of KOH/XOH | % of [DCH] | % of decrease |
|---|---|---|---|
| KOH (100%, reference experiment) | 100/0 | 0.1812 | x |
| N(CH$_3$)$_4$OH | 80/20 | 0.1380 | −24% |
| | 50/50 | 0.1763 | −2.7% |

Example 8: Deactivation of the Catalyst

The procedure of example 3 was followed for each experiment. The catalytic activity of used nickel raney catalyst are reported in Table 5 below and compared to initial activity (111×10$^{-5}$ mol H$_2$/g$_{catalyst}$/s).

6

TABLE 5

| Co-catalyst | % mol of KOH/XOH | Final activity (10$^{-5}$ molH$_2$/g/s) | Activity loss (%) |
|---|---|---|---|
| KOH (100%, reference experiment) | 100/0 | 44.6 | −60% |
| CsOH | 80/20 | 44.7 | −58% |
| N(CH$_3$)$_4$OH | 80/20 | 61.4 | −43% |
| | 50/50 | 55.3 | −45% |
| Ba(OH)$_2$ | 80/20 | 33.8 | −73% |
| NH$_4$OH | 80/20 | 46.3 | −51% |
| N(CH$_3$CH$_2$CH$_2$CH$_2$)$_4$OH | 80/20 | 51.9 | −45% |
| N(CH$_3$)$_3$BzOH | 80/20 | 38.4 | −46% |

The catalyst is less deactivated using the new co-catalyst N(CH$_3$)$_4$OH and N(CH$_3$CH$_2$CH$_2$CH$_2$)$_4$OH.

The invention claimed is:

1. A process for the preparation of hexamethylenediamine by hydrogenation of adiponitrile in the presence of a Raney nickel catalyst and a basic co-catalyst containing potassium hydroxide, wherein the basic co-catalyst contains a further basic compound selected from the group consisting of alkaline hydroxides, alkaline earth hydroxides and ammonium hydroxides, wherein the alkaline hydroxides contain cesium hydroxide, wherein the alkaline earth hydroxides contain barium hydroxide, and wherein the ammonium hydroxides contain an ammonium hydroxide of the general formula NR$_4$OH, wherein each R is independently from each other an alkyl group having from 1 to 16 carbon atoms.

2. The process according to claim 1, wherein the basic co-catalyst contains barium hydroxide Ba(OH)$_2$.

3. The process according to claim 1, wherein the basic co-catalyst contains cesium hydroxide.

4. The process according to claim 1, wherein each R is independently from each other an alkyl group having from 1 to 4 carbon atoms.

5. The process according to claim 4, wherein each R is independently from each other methyl or butyl.

6. The process according to claim 5, wherein R is methyl.

7. The process according to claim 5, wherein R is n-butyl.

8. The process according to claim 1, wherein the basic co-catalyst contains from 50 to 95 mol-% of KOH and from 5 to 50 mol-% of the further basic compound.

9. The process according claim 1, wherein the basic co-catalyst contains from 70 to 90 mol-% of KOH and from 10 to 30 mol-% of the further basic compound.

10. The process according to claim 9, wherein the basic co-catalyst contains from 75 to 85 mol-% of KOH and from 15 to 25 mol-% of the further basic compound.

11. The process according to claim 1, wherein the basic co-catalyst is present in an amount of from 0.1 to 2.0 mol OH$^-$/kg Ni.

12. The process according to claim 1, wherein the hydrogenation is carried out in hexamethylenediamine as solvent containing from 1 to 20% by weight of an aqueous solution of the basic co-catalyst.

13. The process according to claim 1, wherein the hydrogenation is carried out at a temperature of from 50 to 150° C. at a hydrogen pressure of from 1 to 100 bar.

14. The process according to claim 1, wherein the Raney nickel catalyst optionally comprises one or more dopants selected from chromium, titanium, molybdenum, tungsten, manganese, vanadium, zirconium, iron, and zinc.

* * * * *